US008658358B1

(12) United States Patent
Salisbury et al.

(10) Patent No.: US 8,658,358 B1
(45) Date of Patent: Feb. 25, 2014

(54) MUTATIONS ASSOCIATED WITH LONG QT SYNDROME

(75) Inventors: Benjamin Salisbury, Dayton, OH (US); Carole L. Harris-Kerr, North Haven, CT (US)

(73) Assignee: Transgenomic, Inc., Omaha, NE (US)

( * ) Notice: Subject to any disclaimer, the term of this patent is extended or adjusted under 35 U.S.C. 154(b) by 433 days.

(21) Appl. No.: 12/764,841

(22) Filed: Apr. 21, 2010

Related U.S. Application Data

(60) Provisional application No. 61/214,239, filed on Apr. 21, 2009.

(51) Int. Cl.
*C12Q 1/68* (2006.01)
(52) U.S. Cl.
USPC .......................................................... 435/6.1
(58) Field of Classification Search
None
See application file for complete search history.

(56) References Cited

U.S. PATENT DOCUMENTS

2005/0142591 A1    6/2005   Ackerman

OTHER PUBLICATIONS

Tester, David J., et al. Compendium of cardiac channel mutations in 541 consecutive unrelated patients referred for long QT syndrome genetic testing; Heart Rhythm; May 2005, vol. 2 (5):507-17.
Napolitano, Carlo, et al. Genetic Testing in the Long QT Syndrome: development and validation of an efficient approach to genotyping in clinical practice. JAMA. Dec. 21, 2005; vol. 294 (23):2975-80.
Asada, Ken, et al. Redox- and Calmodulin-Dependent S-Nitrosylantion of the KCNQ1 Channel, J Biol Chem. Feb. 27, 2009;284(9):6014-20.

*Primary Examiner* — Juliet Switzer
(74) *Attorney, Agent, or Firm* — McCarter & English, LLP; Jill Mello

(57) ABSTRACT

The invention is based, at least in part, on the observation that the presence of particular biomarkers, e.g., particular mutations in any of the KCNQ1, KCNH2, SCN5A, KCNE1 and KCNE2 genes as identified in Tables 1-5 (and, in particular, those identified with an asterisk), is associated with Long QT Syndrome (LQTS).

4 Claims, No Drawings

MUTATIONS ASSOCIATED WITH LONG QT SYNDROME

RELATED APPLICATIONS

This application claims priority to U.S. Provisional Application No. 61/214,239, filed Apr. 21, 2009, the entire contents of which are hereby incorporated by reference.

SUBMISSION ON COMPACT DISC

This application incorporates by reference the ASCII text file identified by the name 118553-21901 ST25.txt, containing 1.02 MB of data, created on Jun. 6, 2010 and filed in computer-readable format (CRF).

BACKGROUND OF THE INVENTION

The measurement of the contraction of the heart on an electrocardiogram (ECG) produces a waveform with characteristic elements which correspond to the various stages of contraction. One feature of an ECG is referred to as the QT interval, which represents the time period between the initiation of ventricular depolarization and completion of repolarization. The QT interval varies with the heart rate, age and gender. For example, the QT interval decreases with increasing heart rate. Men generally have shorter QT intervals than women.

Under certain circumstances, the QT interval can be prolonged, increasing the risk of a potentially fatal cardiac arrhythmia, resulting in the inability of the heart to contract effectively, which leads to a decrease in blood flow to periphery, including the brain, and syncope or sudden death. In rare cases, a prolonged QT interval is congenital and usually inherited. In other cases, prolongation of the QT interval is the result of a neurological disorder, such as stroke. Most frequently, a prolonged QT interval is caused by certain medications.

Congenital long QT syndrome (LQTS) comprises a distinct group of cardiac channelopathies characterized by QT prolongation on a 12-lead surface electrocardiogram (ECG) and increased risk for syncope, seizures, and sudden cardiac death (SCD) in the setting of a structurally normal heart and otherwise healthy individual. The incidence of LQTS may be as high as 1 in 2500 persons.

Because 2.5% of healthy individuals have a prolonged QT interval and 10-15% of LQTS patients have a normal QT interval, LQTS is not easily diagnosed and subsequently treated.

SUMMARY OF THE INVENTION

The invention is based, at least in part, on the observation that the presence of particular biomarkers, e.g., particular mutations in any of the KCNQ1, KCNH2, SCN5A, KCNE1 and KCNE2 genes as identified in Tables 1-5 (and, in particular, those identified with an asterisk), are associated with Long QT Syndrome (LQTS). Accordingly, the present invention provides methods and compositions for identifying subjects having or susceptible to having LQTS. In addition, the present invention provides methods and compositions for predicting the responsiveness of a subject having or predisposed to having LQTS, e.g., a human subject, to treatment for LQTS therapy. The methods include determining the presence or absence of the biomarkers in a biological sample obtained from the subject, wherein the presence of at least one of the biomarkers as set forth in any of Tables 1-5 is an indication that the subject will respond to LQTS therapy, thereby predicting responsiveness of the subject to the LQTS therapy.

The present invention provides a method for identifying whether a subject suffers from or is predisposed to suffer from congenital long QT syndrome (LQTS). In one aspect, the method for identifying whether a subject suffers from or is predisposed to suffer from congenital long QT syndrome (LQTS) includes identifying the presence of at least one biomarker in a biological sample obtained from the subject, wherein the biomarker is selected from the group consisting of variants set forth in Tables 1-5.

In one embodiment, the biomarker is a variant in at least one of the KCNQ1 (LQT1), KCNH2 (LQT2), SCN5A (LQT3), KCNE1 or KCNE2 genes. In another embodiment, the variant is selected from the group consisting of a mutation, a missense mutation, a nonsense mutation, an insertion, a deletion, or a frameshift mutation. In another embodiment, the variant disrupts the open reading frame of the KCNQ1, KCNH2, SCN5A, KCNE1 or KCNE2 genes. In another embodiment, the variant disrupts the canonical splice site of the KCNQ1, KCNH2, SCN5A, KCNE1 or KCNE2 genes. In another embodiment, the variant disrupts the splice acceptor sequence of the KCNQ1, KCNH2, SCN5A, KCNE1 or KCNE2 genes. In another embodiment, the variant disrupts the splice donor recognition sequence of the KCNQ1, KCNH2, SCN5A, KCNE1 or KCNE2 genes. In yet another embodiment, the biomarker is a L266P mutation in KCNQ1, a R518X mutation in KCNQ1, a R594Q mutation in KCNQ1, a G168R mutation in KCNQ1 or a E1784K mutation in SCN5A. In certain embodiments, the biomarker is a nonsense mutation in SCN5A selected from the group consisting of Q73X, R179X, R222X, Y389X and W1798X. In another embodiment, the biomarker is a frameshift mutation in SCN5A selected from the group consisting of V850fs+18X and L1786fs+45X.

The present invention also provides a method for predicting therapeutic responsiveness of a subject having LQTS or susceptible to having LQTS to LQTS therapy. In one aspect, the method includes determining the presence or absence of at least one biomarker in a biological sample obtained from the subject, wherein the biomarker is selected from the group consisting of variants set forth in Tables 1-5, and wherein the presence of the at least one biomarker in the sample is an indication that the subject will respond to the LQTS therapy, thereby predicting responsiveness of the subject to the LQTS therapy.

In one embodiment, the LQTS therapy includes a method selected from the group consisting of administration of beta receptor blocking agents, implantation of an implantable cardioverter-defibrillator (ICD), potassium supplementation, administration of a sodium channel blocker such as mexiletine, and amputation of the cervical sympathetic chain.

In one embodiment, determining the presence or absence of at least one biomarker is accomplished using a technique selected from the group consisting of polymerase chain reaction (PCR) amplification reaction, reverse-transcriptase PCR analysis, single-strand conformation polymorphism analysis (SSCP), mismatch cleavage detection, heteroduplex analysis, Southern blot analysis, Western blot analysis, deoxyribonucleic acid sequencing, restriction fragment length polymorphism analysis, haplotype analysis, serotyping, and combinations or sub-combinations thereof, of said sample. In one embodiment, the sample comprises a fluid obtained from the subject. For example, the fluid may be a blood fluid, vomit, intra-articular fluid, saliva, lymph, cystic fluid, urine, fluid collected by bronchial lavage, fluid collected by peritoneal rinsing, or gynecological fluid. In another embodiment, the sample is a blood sample or a component thereof. In another embodiment, the sample comprises a tissue or component thereof obtained from the subject. For example, the tissue may be bone, connective tissue, cartilage, lung, liver, kidney, muscle tissue, heart, pancreas, or skin. In one embodiment, the subject is a human.

In one embodiment, the biomarker is a variant in at least one of the KCNQ1 (LQT1), KCNH2 (LQT2), SCN5A (LQT3), KCNE1 or KCNE2 genes. In another embodiment, the variant is selected from the group consisting of a mutation, a missense mutation, a nonsense mutation, an insertion, a deletion, or a frameshift mutation. In another embodiment, the variant disrupts the open reading frame of the KCNQ1, KCNH2, SCN5A, KCNE1 or KCNE2 genes. In another embodiment, the variant disrupts the canonical splice site of the KCNQ1, KCNH2, SCN5A, KCNE1 or KCNE2 genes. In another embodiment, the variant disrupts the splice acceptor sequence of the KCNQ1, KCNH2, SCN5A, KCNE1 or KCNE2 genes. In another embodiment, the variant disrupts the splice donor recognition sequence of the KCNQ1, KCNH2, SCN5A, KCNE1 or KCNE2 genes. In yet another embodiment, the biomarker is a L266P mutation in KCNQ1, a R518X mutation in KCNQ1, a R594Q mutation in KCNQ1, a G168R mutation in KCNQ1 or a E1784K mutation in SCN5A. In certain embodiments, the biomarker is a nonsense mutation in SCN5A selected from the group consisting of Q73X, R179X, R222X, Y389X and W1798X. In another embodiment, the biomarker is a frameshift mutation in SCN5A selected from the group consisting of V850fs+18X and L1786fs+45X.

The present invention also provides a kit for predicting responsiveness of a subject having LQTS or susceptible to having LQTS to LQTS therapy. In one aspect, the kit includes means for determining the presence or absence of at least one biomarker in a biological sample obtained from the subject, wherein the biomarker is selected from the group consisting of variants set forth in Tables 1-5, and instructions for use of the kit to predict responsiveness of the subject having LQTS to LQTS therapy. In one embodiment, the kit further includes means for obtaining a biological sample from a subject. In another embodiment, the kit further includes a control sample, for example, a nucleic acid molecule encoding any of SEQ ID NOs:1-5.

The present invention also provides a nucleic acid molecule including a variant of the KCNQ1 (LQT1), KCNH2 (LQT2), SCN5A (LQT3), KCNE1 or KCNE2 genes selected from the group consisting of the variants set forth in Tables 1-5.

DETAILED DESCRIPTION OF THE INVENTION

The invention is based, at least in part, on the observation that the presence of particular biomarkers, e.g., particular mutations in any of the KCNQ1, KCNH2, SCN5A, KCNE1 and KCNE2 genes as identified in Tables 1-5 (and, in particular, those identified with an asterisk), are associated with Long QT Syndrome (LQTS). Accordingly, the present invention provides methods and compositions for identifying subjects having or susceptible to having LQTS. Specifically, by identifying the variants of the KCNQ1, KCNH2, SCN5A, KCNE1 and KCNE2 genes disclosed herein in biological samples derived from a subject, one can identify the subject as having or predisposed to having LQTS.

In addition, the present invention provides methods and compositions for predicting the responsiveness of a subject having or predisposed to having LQTS, e.g., a human subject, to treatment for LQTS therapy. The methods include determining the presence or absence of the biomarkers in a biological sample obtained from the subject, wherein the presence of at least one of the biomarkers as set forth in any of Tables 1-5 is an indication that the subject will respond to LQTS therapy, thereby predicting responsiveness of the subject to the LQTS therapy.

In order that the present invention may be more readily understood, certain terms are first defined.

As used herein, the term "long QT syndrome" or "LQTS" refers to a rare inborn heart condition in which delayed repolarization of the heart following a heartbeat increases the risk of episodes of torsade de pointes (a form of irregular heartbeat that originates from the ventricles). These episodes may lead to palpitations, fainting and sudden death due to ventricular fibrillation. Episodes may be provoked by various stimuli, depending on the subtype of the condition.

As used herein, the term "biomarker" is intended to encompass an indicator of a biologic state and includes genes (and nucleotide sequences of such genes), mRNAs (and nucleotide sequences of such mRNAs) and proteins (and amino acid sequences of such proteins). A "biomarker expression pattern" is intended to refer to a quantitative or qualitative summary of the expression of one or more biomarkers in a subject, such as in comparison to a standard or a control.

As used herein, biomarkers encompass variants of the KCNQ1, KCNH2, SCN5A, KCNE1 and KCNE2 genes as set forth in Tables 1-5. For example, biomarkers include mutations, missense mutations, nonsense mutations, insertions, deletions, or frameshift mutations in at least one of these genes. The biomarkers may serve to disrupt the open reading frame of the KCNQ1, KCNH2, SCN5A, KCNE1 or KCNE2 genes and/or the canonical splice site, for example, the splice acceptor sequence or splice donor recognition sequences, of the KCNQ1, KCNH2, SCN5A, KCNE1 or KCNE2 genes.

In particular embodiments, the biomarker is any one of a L266P mutation in KCNQ1, a R518X mutation in KCNQ1, a R594Q mutation in KCNQ1, a G168R mutation in KCNQ1, or a E1784K mutation in SCN5A. Alternatively or in addition, the biomarker may be a nonsense mutation in SCN5A selected from the group consisting of Q73X, R179X, R222X, Y389X and W1798X. In other embodiments, the biomarker may be a frameshift mutation in SCN5A selected from the group consisting of V850fs+18X and L1786fs+45X.

The terms "increased" or "increased expression" and "decreased" or "decreased expression", with respect to the expression pattern of a biomarker(s), are used herein as meaning that the level of expression is increased or decreased relative to a constant basal level of expression of a household, or housekeeping, gene, whose expression level does not significantly vary under different conditions. A nonlimiting example of such a household, or housekeeping, gene is GAPDH. Other suitable household, or housekeeping, genes are well-established in the art.

As set forth below, the KCNQ1, KCNH2, SCN5A, KCNE1 or KCNE2 genes generally encode the major pore-forming alpha subunits of the macromolecular channel complexes Kv7.1 ($I_{KS}$), Kv11.1 ($I_{Kr}$) and Nav1.5 ($I_{Na}$).

As used herein, the term KCNQ1 (LQT1) refers to the gene encoding the voltage-gated potassium channel KvLQT1 that is highly expressed in the heart. It is believed that the product of the KCNQ1 gene produces an alpha subunit that interacts with other proteins (particularly the minK beta subunit) to create the $I_{Ks}$ ion channel, which is responsible for the delayed potassium rectifier current of the cardiac action potential. The KCNQ1 gene has been isolated to chromosome 11p15.5. The nucleotide sequence for KCNQ1 is set forth in SEQ ID NO:1.

As used herein, the term KCNH2 (LQT2), also known as human ether-a-go-go related gene (HERG), on chromosome 7 is part of the rapid component of the potassium rectifying current (W. The $I_{Kr}$ current is mainly responsible for the termination of the cardiac action potential, and therefore the length of the QT interval. Normally functioning HERG gene allows protection against early after depolarizations (EADs). Specifically, KCNH2 refers to the gene encoding potassium voltage-gated channel, subfamily H (eag-related), member 2. The nucleotide sequence for KCNH2 is set forth in SEQ ID NO:2.

As used herein, the term SCN5A (LQT3) (also hH1 and $Na_v1.5$) refers to the gene encoding sodium channel, voltage-gated, type V, alpha subunit. This gene is located on chromosome 3p21-24, and is known as SCN5A. The nucleotide sequence for SCN5A is set forth in SEQ ID NO:3. The mutations slow the inactivation of the $Na^+$ channel, resulting in prolongation of the $Na^+$ influx during depolarization. Paradoxically, the mutant sodium channels inactivate more quickly, and may open repetitively during the action potential.

As used herein, the term KCNE1 refers to the gene encoding potassium voltage-gated channel, Isk-related family, member 1 (potassium channel beta subunit MinK) The nucleotide sequence for KCNE1 is set forth in SEQ ID NO:4.

As used herein, the term KCNE2 refers to the gene encoding potassium voltage-gated channel, Isk-related family, member 2 (potassium channel beta subunit MiRP1, constituting part of the $I_{Kr}$ repolarizing $K^+$ current). The nucleotide sequence for KCNE2 is set forth in SEQ ID NO:5.

As used herein, the term "subject" includes humans, and non-human animals amenable to LQTS therapy, e.g., preferably mammals, such as non-human primates, sheep, dogs, cats, horses and cows.

As used herein, the term "treatment regimen" is intended to refer to one or more parameters selected for the treatment of a subject, e.g., by administering beta receptor blocking agents, which parameters can include, but are not necessarily limited to, the type of agent chosen for administration, the dosage, the formulation, the route of administration and the frequency of administration.

LQTS therapy includes, but is not limited to, administration of beta receptor blocking agents, implantation of an implantable cardioverter-defibrillator (ICD), potassium supplementation, administration of a sodium channel blocker such as mexiletine, and amputation of the cervical sympathetic chain.

The term "predicting responsiveness to LQTS therapy", as used herein, is intended to refer to an ability to assess the likelihood that treatment of a subject with LQTS therapy will or will not be effective in (e.g., provide a measurable benefit to) the subject. In particular, such an ability to assess the likelihood that treatment will or will not be effective typically is exercised before LQTS treatment is begun in the subject.

However, it is also possible that such an ability to assess the likelihood that treatment will or will not be effective can be exercised after treatment has begun but before an indicator of effectiveness (e.g., an indicator of measurable benefit) has been observed in the subject.

The present invention is further illustrated by the following examples which should not be construed as further limiting. The contents of all references, patents and published patent applications cited throughout this application are expressly incorporated herein by reference in their entirety.

EXAMPLES

Example 1

Identification of Biomarkers Associated with LQTS

Between May 2004 and October 2008, 2500 unrelated patients (1515 females, average age at testing=26±17 years and 985 males, average age at testing=19±15 years) were tested for LQTS by PGxHealth, LLC in New Haven, Conn. Patient genomic DNA was analyzed for mutations in all 60 translated exons and their canonical splice site regions of KCNQ1, KCNH2, SCN5A, KCNE1, and KCNE2 using polymerase chain reaction (PCR) and automated DNA sequencing. All PCR primers were designed with special care to avoid the phenomenon of allelic dropout, which can lead to a false negative genetic test result. Insertions and deletions that span an amplicon or interfere with amplification are not detected. Reference sequences for KCNQ1, KCNH2, SCN5A, KCNE1, and KCNE2 are provided as, respectively, SEQ ID NO:1, SEQ ID NO:2, SEQ ID NO:3, SEQ ID NO:4, and SEQ ID NO:5.

All putative LQTS-associated mutations and other variants were denoted using known and accepted nomenclature. For example, the single letter amino acid code was used to designate missense mutations (single amino acid substitutions) using the L250P format. Here, at amino acid position 250, the 'wild type' amino acid (L=leucine) is replaced by a proline (P) on one of the chromosomes. Frameshift mutations resulting from nucleotide insertions or deletions were annotated using the R174fs+105X format. Here, R174 represents the last properly encoded amino acid followed by a frameshift (fs) in the coding sequence resulting in 105 miscoded amino acids prior to reaching a stop codon (X) resulting in a truncated protein containing a total of 279 amino acids.

A substitution of either the first two or the last two nucleotides of a particular exon has the capacity to alter proper mRNA splicing, regardless of whether the nucleotide substitution codes for a different amino acid (missense mutation), produces a stop codon (nonsense mutation) or does not alter the open reading frame at all (i.e., a synonymous or silent single nucleotide substitution). As such, mutations involving this exonic portion of the "splice site" were considered as possible splicing mutations in this study and annotated as either "missense/splice," "nonsense/splice," or "silent/splice" mutations in order to distinguish them from intronic mutations predicted to disrupt splicing.

Topological placement of the mutations was done using a combination of Swissprot (http://ca.expasy.org/uniprot/) and recent studies of the linear topologies for each of the three main pore-forming alpha subunits. The Swissprot database provides generally accepted residue ranges corresponding with each ion-channel region and specialized sub-regions. To be considered as a potential LQTS-causing mutation, the variant should disrupt the open reading frame (i.e., missense, nonsense, insertion/deletion, or frameshift mutations) or the canonical splice site (splice acceptor or splice donor recognition sequences). In addition to the exonic splice sites described above, the canonical acceptor splice site was defined as the seven intronic nucleotides, except the fourth, preceding an exon (designated as IVS−1, −2, −3, −5, −6, or −7) and the donor splice site as the first five intronic nucleotides following an exon (designated as IVS+1, +2, +3, +4, or +5). Hence, single nucleotide substitutions that did not change the open reading frame (i.e., synonymous single nucleotide polymorphisms/variants) and intronic nucleotide substitutions located outside of the canonical splice site recognition sequence (i.e., beyond IVS−5 or IVS+5) were excluded from consideration.

Additionally, the candidate mutation must not have been observed in a panel of now over 1300 ostensibly healthy volunteers (>2600 reference alleles). As such, the sole or concurrent presence of common or rare non-synonymous single nucleotide polymorphisms like P448R-KCNQ1, R176W-KCNH2, H558R-SCN5A, D85N-KCNE1, or Q9E-KCNE2 would not be designated as a pathogenic mutation resulting in LQT1, LQT2, LQT3, LQT5, or LQT6 respectively, despite there being evidence of slight abnormality or risk associated with some of these. Further, such polymorphisms would not be counted towards the assignment of compound or multiple mutation status to an individual.

The genes causative of the major LQTS subtypes encode ion channel subunits with regions that span the cell membrane to allow ions to flow in or out of the cell, as well as functional domains that regulate the passage of these ions. The probability that a novel missense mutation identified in a LQTS patient is pathogenic is directly related to the position of the mutation within the protein. The protein encoded by KCNQ1 has a transmembrane domain region that consist of 6 transmembrane spanning domains annotated S1 through S6, and each domain is connected by a small linker region named according the domains that it connects (i.e., the first linker domain is named S1/S2). The entire transmembrane domain region of KCNQ1 protein is flanked by non-transmembrane regions referred to as the N-terminus and C-terminus. Within the C-terminus region of KCNQ1, a regulatory domain called the Subunit Assembly Region (SAR) exists. Similar for the proteins encoded by KCNH2, SCN5A, KCNE1, and KCNE2, transmembrane domain regions are also flanked by N-termini and C-termini. Specifically, KCNH2 protein has 6 transmembrane spanning domains referred to S1 through S6, linker domains connecting theses transmembrane spanning domains, regulatory domains within the N-terminus called the Per-Arnt-Sim (PAS) domain and the PAS-associated C-terminal domain (PAC), and one regulatory domain within the C-terminus called the Cyclic nucleotide binding domain (cNBD). The protein region in KCNH2 that is located between and including the S5 and S6 transmembrane domains is specifically referred to as the Pore region. SCN5A protein consists of 4 sets of the 6 transmembrane spanning domains referred to as DI through DIV and linker domains connecting each transmembrane spanning segment. The proteins encoded by KCNE1 and KCNE1 each contain a single transmembrane domain flanked by N- and C-termini. The specific location of a mutation in the complex of structure of these LQTS causative genes is directly related to the likelihood of its pathogenicity. Missense mutations that localize to the pore domain, transmembrane-spanning domains (e.g. S1-S6), or other critical subdomains (i.e., PAS, PAC, cNBD, and SAR) confer a high probability for causing LQTS.

Overall, 903/2500 (36%) unrelated cases had a positive genetic test with the identification of a putative LQTS-causing mutation that was absent in over 2600 reference alleles. Among the 903 genotype-positive patients, 821 (91%) had a single mutation: 386 in KCNQ1 (43%), 288 in KCNH2 (32%), 115 in SCN5A (13%), 24 in KCNE1, and 8 in KCNE2.

The remaining 82 patients (9%) had >1 mutation including 30 cases with multiple mutations in the same gene: KCNQ1 (19), KCNH2 (3), SCN5A (6), KCNE1 (1), and KCNE2 (1). Fifty-two cases were compound heterozygous with mutations in >1 gene.

In total, the 903 genotype-positive cases stemmed from 562 distinct LQTS-causing mutations: 199 distinct mutations in KCNQ1, 226 in KCNH2, 110 in SCN5A, 18 in KCNE1, and 9 in KCNE2 (Tables 1-5). Notably, over half of the mutations (336/562, 60%) were novel to this cohort including 92 in KCNQ1, 159 in KCNH2, and 70 in SCN5A. The vast majority (76%) of the mutations were observed in a single index case while 134 mutations (24%) were observed more than once in this cohort. The five most commonly observed LQTS-causing mutations were L266P-KCNQ1 seen in 30 unrelated patients, R518X-KCNQ1 in 24, R594Q-KCNQ1 in fifteen, G168R-KCNQ1 in fifteen, and E1784K-SCN5A in fifteen unrelated patients.

Overall, the majority of mutations (394/562, 70%) were missense, while 85 (15%) were frame-shift mutations, 33 (5.9%) involved canonical splice sites, 33 (5.9%) were nonsense mutations, and 17 (3%) were in-frame insertions/deletions. While 64% of all frame-shift mutations were identified in KCNH2 (representing 24% of all KCNH2 mutations), 76% of the splice-site mutations involved KCNQ1 (representing 12.5% of all KCNQ1 mutations). As will be discussed below, five nonsense (Q73X, R179X, R222X, Y389X, and W1798X) and two frame-shift mutations (V850fs+18X and L1786fs+45X) were identified in SCN5A.

For mutations in KCNQ1, 102/199 (51%) localized to the transmembrane spanning and pore-forming domains, thirteen (6.5%) to the specialized Subunit Assembly Region, 15 (7.5%) in the N-terminus, and 69 (35%) resided in the C-terminus (Table 1). For mutations in KCNH2, 73/226 (32%) localized to the transmembrane spanning and pore-forming domains, 18 (8%) in the N-terminal PAS/PAC regulatory domains, 47 (21%) elsewhere in the N-terminus, 18 (8%) in the C-terminal cyclic nucleotide domain (cNBD), and 70 (31%) elsewhere in the C-terminus (Table 2). Among the 108 mutations in SCN5A, eleven (10%) localized to the N-terminus, 46 (43%) to the transmembrane spanning and pore-forming domains, 38 (35%) to the inter-domain cytoplasmic linkers (DI-DII, DII-DIII, and DIII-DIV), and thirteen (12%) to the C-terminus (Table 3).

TABLE 1

Summary of putative LQT1-associated mutations in KCNQ1

| Region | Nucleotide | Variant | Position in SEQ ID NO: 1 | Mutation Type | Location | No. of patients |
|--------|-----------|---------|--------------------------|---------------|----------|-----------------|
| Exon 1 | 5 C > T | A2V* | 80533 | Missense | N-Terminal | 1 |
| Exon 1 | 19 C > T | P7S* | 80547 | Missense | N-Terminal | 1 |
| Exon 1 | 108insT | F36fs + 247X* | 80636 | Frame shift | N-Terminal | 1 |
| Exon 1 | 136 G > A | A46T | 80664 | Missense | N-Terminal | 2 |
| Exon 1 | 153 C > G | Y51X | 80681 | Nonsense | N-Terminal | 1 |
| Exon 1 | 176delC | A58fs + 26X* | 80704 | Frame shift | N-Terminal | 1 |

TABLE 1-continued

Summary of putative LQT1-associated mutations in KCNQ1

| Region | Nucleotide | Variant | Position in SEQ ID NO: 1 | Mutation Type | Location | No. of patients |
|---|---|---|---|---|---|---|
| Exon 1 | 190_210del | 64_70del | Del: 80718 to 80738 | In-frame del | N-Terminal | 3 |
| Exon 1 | 197 C > T | S66F* | 80725 | Missense | N-Terminal | 1 |
| Exon 1 | 200_210del | S66fs + 213X* | Del: 80728 to 80738 | Frame shift | N-Terminal | 1 |
| Exon 1 | 217 C > A | P73T | 80745 | Missense | N-Terminal | 4 |
| Exon 1 | 242_264del; insGCGCC CGCGG (SEQ ID NO: 6) | G80fs + 151X* | Del: 80770 to 80792 Ins: SEQ ID NO: 6 | Frame shift | N-Terminal | 1 |
| Exon 1 | 273_299del; insGG | V91fs + 136X* | Del: 80801 to 80827 Ins: GG | Frame shift | N-Terminal | 1 |
| Exon 1 | 332 A > G | Y111C | 80860 | Missense | N-Terminal | 5 |
| Exon 1 | 350 C > T | P117L | 80878 | Missense | N-Terminal | 1 |
| Exon 1 | 365insT | K121fs + 162X* | 80893 | Frame shift | N-Terminal | 2 |
| Exon 1 | 381 C > A | F127L* | 80909 | Missense | S1 Domain | 1 |
| Intron 1 | 386 + 1 G > A | | 80915 | Splice site | S1 Domain | 1 |
| Exon 2 | 397 G > A | V133I | 163375 | Missense | S1 Domain | 1 |
| Exon 2 | 401 T > C | L134P* | 163379 | Missense | S1 Domain | 1 |
| Exon 2 | 403delG | L134fs + 101X* | 163381 | Frame shift | S1 Domain | 1 |
| Exon 2 | 430 A > G | T144A | 163408 | Missense | S1/S2 | 1 |
| Exon 2 | 451_452delCT | A150fs + 132X | 163429 | Frame shift | S2 Domain | 1 |
| Exon 2 | 458 C > T | T153M* | 163436 | Missense | S2 Domain | 1 |
| Intron 2 | 477 + 1 G > A | | 163456 | Splice site | S2 Domain | 1 |
| Intron 2 | 477 + 5 G > C | | 163460 | Splice site | S2 Domain | 1 |
| Intron 2 | 477 + 5 G > A | | 163460 | Splice site | S2 Domain | 4 |
| Exon 3 | 479 A > T | E160V* | 206043 | Missense/Splice | S2 Domain | 1 |
| Exon 3 | 484 G > A | V162M* | 206048 | Missense | S2 Domain | 1 |
| Exon 3 | 488delT | V162fs + 73X | 206052 | Frame shift | S2 Domain | 1 |
| Exon 3 | 502 G > A | G168R | 206066 | Missense | S2 Domain | 15 |
| Exon 3 | 502 G > C | G168R | 206066 | Missense | S2 Domain | 4 |
| Exon 3 | 504delG | G168fs + 67X* | 206068 | Frame shift | S2 Domain | 1 |
| Exon 3 | 513 C > G | Y171X | 206077 | Nonsense | S2/S3 | 1 |
| Exon 3 | 514 G > A | V172M | 206078 | Missense | S2/S3 | 2 |
| Exon 3 | 520 C > T | R174C | 206084 | Missense | S2/S3 | 1 |
| Exon 3 | 521 G > A | R174H | 206085 | Missense | S2/S3 | 1 |
| Exon 3 | 524_534del | R174fs + 105X* | Del: 206088 to 206098 | Frame shift | S2/S3 | 1 |
| Exon 3 | 532 G > A | A178T | 206096 | Missense | S2/S3 | 1 |
| Exon 3 | 535 G > A | G179S | 206099 | Missense | S2/S3 | 2 |
| Exon 3 | 550 T > C | Y184H* | 206114 | Missense | S2/S3 | 1 |
| Exon 3 | 556 G > C | G186R* | 206120 | Missense | S2/S3 | 1 |
| Exon 3 | 564 G > A | W188X* | 206128 | Nonsense | S2/S3 | 1 |
| Exon 3 | 569 G > A | R190Q | 206133 | Missense | S2/S3 | 3 |
| Exon 3 | 569 G > T | R190L* | 206133 | Missense | S2/S3 | 1 |
| Exon 3 | 573_577delGCGCT | L191fs + 90X | 206137 | Frame shift | S2/S3 | 4 |
| Exon 3 | 583 C > T | R195W* | 206147 | Missense | S2/S3 | 2 |
| Exon 3 | 585delG | R195fs + 40X | 206149 | Frame shift | S2/S3 | 4 |
| Exon 3 | 592 A > G | I198V* | 206156 | Missense | S3 Domain | 1 |
| Exon 3 | 595 T > G | S199A* | 206159 | Missense | S3 Domain | 1 |
| Exon 3 | 604 G > A | D202N | 206168 | Missense/Splice | S3 Domain | 1 |
| Intron 3 | 605 − 2 A > G | | 206737 | Splice site | S3 Domain | 1 |
| Exon 4 | 612 C > G | I204M | 206746 | Missense | S3 Domain | 1 |
| Exon 4 | 643 G > A | V215M | 206777 | Missense | S3 Domain | 1 |
| Exon 4 | 671 C > T | T224M* | 206805 | Missense | S3/S4 | 1 |
| Exon 4 | 674 C > T | S225L | 206808 | Missense | S3/S4 | 8 |
| Exon 5 | 691 C > T | R231C | 207434 | Missense | S4 Domain | 1 |
| Exon 5 | 692 G > A | R231H | 207435 | Missense | S4 Domain | 1 |
| Exon 5 | 704 T > A | I235N | 207447 | Missense | S4 Domain | 2 |
| Exon 5 | 722 T > G | V241G* | 207465 | Missense | S4 Domain | 1 |
| Exon 5 | 724 G > A | D242N | 207467 | Missense | S4 Domain | 4 |
| Exon 5 | 727delC | D242fs + 19X* | 207470 | Frame shift | S4 Domain | 1 |
| Exon 5 | 727 C > T | R243C | 207470 | Missense | S4 Domain | 1 |
| Exon 5 | 749 T > C | L250P* | 207492 | Missense | S4/S5 | 1 |
| Exon 5 | 760 G > A | V254M | 207503 | Missense | S4/S5 | 10 |
| Exon 5 | 775 C > T | R259C | 207518 | Missense | S4/S5 | 5 |
| Exon 5 | 776_780dupCCACC | H258fs + 5X* | 207519 | Frame shift | S4/S5 | 1 |
| Exon 5 | 776 G > T | R259L | 207519 | Missense | S4/S5 | 1 |
| Exon 6 | 781 G > C | E261Q* | 208260 | Missense/Splice | S4/S5 | 1 |
| Exon 6 | 781 G > T | E261X* | 208260 | Nonsense/Splice | S4/S5 | 1 |
| Exon 6 | 784 C > G | L262V | 208263 | Missense | S5 domain | 1 |
| Exon 6 | 796delC | T265fs + 22X | 208275 | Frame shift | S5 domain | 3 |
| Exon 6 | 797 T > C | L266P | 208276 | Missense | S5 domain | 30 |

TABLE 1-continued

Summary of putative LQT1-associated mutations in KCNQ1

| Region | Nucleotide | Variant | Position in SEQ ID NO: 1 | Mutation Type | Location | No. of patients |
|---|---|---|---|---|---|---|
| Exon 6 | 803 T > G | I268S* | 208282 | Missense | S5 domain | 1 |
| Exon 6 | 805 G > A | G269S | 208284 | Missense | S5 domain | 10 |
| Exon 6 | 806 G > A | G269D | 208285 | Missense | S5 domain | 4 |
| Exon 6 | 815 G > A | G272D | 208294 | Missense | S5 domain | 1 |
| Exon 6 | 817 C > T | L273F | 208296 | Missense | S5 domain | 7 |
| Exon 6 | 820 A > G | I274V | 208299 | Missense | S5 domain | 1 |
| Exon 6 | 829 T > C | S277P* | 208308 | Missense | S5 domain | 1 |
| Exon 6 | 830 C > T | S277L | 208309 | Missense | S5 domain | 2 |
| Exon 6 | 839 T > A | V280E | 208318 | Missense | S5 domain | 1 |
| Exon 6 | 842 A > G | Y281C | 208321 | Missense | S5 domain | 1 |
| Exon 6 | 845 T > C | L282P | 208324 | Missense | S5 domain | 1 |
| Exon 6 | 848 C > G | A283G* | 208327 | Missense | S5/pore | 2 |
| Exon 6 | 862_880del | A287fs + 59X* | Del: 208341 to 208359 | Frame shift | S5/pore | 2 |
| Exon 6 | 875 G > A | G292D | 208354 | Missense | S5/pore | 1 |
| Exon 6 | 877 C > T | R293C | 208356 | Missense | S5/pore | 4 |
| Exon 6 | 905 C > T | A302V | 208384 | Missense | Pore | 1 |
| Exon 6 | 905 C > A | A302E* | 208384 | Missense | Pore | 1 |
| Exon 6 | 908 T > C | L303P* | 208387 | Missense | Pore | 1 |
| Exon 6 | 913 T > C | W305R* | 208392 | Missense | Pore | 1 |
| Exon 6 | 914 G > C | W305S | 208393 | Missense | Pore | 1 |
| Exon 6 | 914 G > A | W305X | 208393 | Nonsense | Pore | 1 |
| Exon 6 | 916 G > A | G306R | 208395 | Missense | Pore | 1 |
| Exon 6 | 916 G > C | G306R | 208395 | Missense | Pore | 1 |
| Exon 7 | 935 C > T | T312I | 218864 | Missense | Pore | 2 |
| Exon 7 | 940 G > A | G314S | 218869 | Missense | Pore | 7 |
| Exon 7 | 940 G > T | G314C | 218869 | Missense | Pore | 1 |
| Exon 7 | 944 A > G | Y315C | 218873 | Missense | Pore | 4 |
| Exon 7 | 947 G > T | G316V* | 218876 | Missense | Pore | 1 |
| Exon 7 | 958 C > T | P320S* | 218887 | Missense | Pore | 1 |
| Exon 7 | 964 A > G | T322A | 218893 | Missense | Pore/S6 | 2 |
| Exon 7 | 965 C > T | T322M | 218894 | Missense | Pore/S6 | 4 |
| Exon 7 | 973 G > A | G325R | 218902 | Missense | Pore/S6 | 6 |
| Exon 7 | 1016 T > A | F339Y* | 218945 | Missense | S6 | 1 |
| Exon 7 | 1017_1019delCTT | 340delF | 218946 | In-frame del | S6 | 1 |
| Exon 7 | 1022 C > A | A341E | 218951 | Missense | S6 | 4 |
| Exon 7 | 1022 C > T | A341V | 218951 | Missense | S6 | 8 |
| Exon 7 | 1022 C > G | A341G* | 218951 | Missense | S6 | 1 |
| Exon 7 | 1024 C > T | L342F | 218953 | Missense | S6 | 2 |
| Exon 7 | 1028 C > T | P343L | 218957 | Missense | S6 | 1 |
| Exon 7 | 1031 C > T | A344V | 218960 | Missense/Splice | S6 | 1 |
| Exon 7 | 1032 G > A | A344A | 218961 | Silent/Splice | S6 | 10 |
| Intron 7 | 1032 + 1 G > T | | 218962 | Splice site | S6 | 1 |
| Intron 7 | 1032 + 1 G > A | | 218962 | Splice site | S6 | 2 |
| Intron 7 | 1032 + 2 T > C | | 218963 | Splice site | S6 | 1 |
| Intron 7 | 1032 + 5 G > T | | 218966 | Splice site | S6 | 1 |
| Exon 8 | 1046 C > A | S349X | 220642 | Nonsense | C-Terminal | 1 |
| Exon 8 | 1048 G > A | G350R | 220644 | Missense | C-Terminal | 1 |
| Exon 8 | 1052 T > C | F351S | 220648 | Missense | C-Terminal | 1 |
| Exon 8 | 1061 A > G | K354R* | 220657 | Missense | C-Terminal | 1 |
| Exon 8 | 1066 C > T | Q356X | 220662 | Nonsense | C-Terminal | 1 |
| Exon 8 | 1075 C > T | Q359X* | 220671 | Nonsense | C-Terminal | 4 |
| Exon 8 | 1079 G > T | R360M* | 220675 | Missense | C-Terminal | 2 |
| Exon 8 | 1085 A > G | K362R | 220681 | Missense | C-Terminal | 5 |
| Exon 8 | 1093 A > C | N365H* | 220689 | Missense | C-Terminal | 1 |
| Exon 8 | 1096 C > T | R366W | 220692 | Missense | C-Terminal | 8 |
| Exon 8 | 1097 G > A | R366Q | 220693 | Missense | C-Terminal | 1 |
| Exon 8 | 1121 T > A | L374H | 220717 | Missense | C-Terminal | 1 |
| Intron 8 | 1128 + 1 G > A | | 220725 | Splice site | C-Terminal | 1 |
| Intron 8 | 1128 + 1 G > T | | 220725 | Splice site | C-Terminal | 1 |
| Intron 8 | 1128 + 5 G > A | | 220729 | Splice site | C-Terminal | 1 |
| Exon 9 | 1135 T > G | W379G* | 222994 | Missense | C-Terminal | 1 |
| Exon 9 | 1153 G > A | E385K* | 223012 | Missense | C-Terminal | 1 |
| Exon 9 | 1165 T > C | S389P* | 223024 | Missense | C-Terminal | 1 |
| Exon 9 | 1171_1173dupCTT | 391dupS* | 223030 | In-frame ins | C-Terminal | 1 |
| Exon 9 | 1177_1179dupTGG | 393dupW* | 223036 | In-frame ins | C-Terminal | 3 |
| Exon 9 | 1189 C > T | R397W | 223048 | Missense | C-Terminal | 3 |
| Exon 9 | 1193 A > G | K398R* | 223052 | Missense | C-Terminal | 1 |
| Exon 9 | 1196_1197delCCinsA | K398fs + 19X* | 223055 | Frame shift | C-Terminal | 1 |
| Exon 9 | 1202insC | P400fs + 61X | 223061 | Frame shift | C-Terminal | 1 |
| Intron 9 | 1251 + 2 T > C | | 223112 | Splice site | C-Terminal | 1 |
| Exon 10 | 1265delA | K421fs + 9X* | 224144 | Frame shift | C-Terminal | 2 |
| Exon 10 | 1338 C > G | D446E* | 224217 | Missense | C-Terminal | 2 |
| Exon 10 | 1343 C > T | P448L* | 224222 | Missense | C-Terminal | 1 |

TABLE 1-continued

Summary of putative LQT1-associated mutations in KCNQ1

| Region | Nucleotide | Variant | Position in SEQ ID NO: 1 | Mutation Type | Location | No. of patients |
|---|---|---|---|---|---|---|
| Exon 10 | 1351 C > T | R451W* | 224230 | Missense | C-Terminal | 1 |
| Exon 10 | 1378 G > A | G460S | 224257 | Missense | C-Terminal | 1 |
| Exon 11 | 1430 C > T | P477L* | 297413 | Missense | C-Terminal | 1 |
| Exon 11 | 1462delG | E487fs + 9X* | 297445 | Frame shift | C-Terminal | 1 |
| Exon 11 | 1486_1487delCT | T495fs + 18X | 297469 | Frame shift | C-Terminal | 1 |
| Exon 11 | 1513 C > T | Q505X* | 297496 | Nonsense/Splice | C-Terminal | 1 |
| Intron 11 | 1515 − 2 delAG | | 404258 | Splice site | C-Terminal | 1 |
| Exon 12 | 1531 C > T | R511W* | 404276 | Missense | C-Terminal | 1 |
| Exon 12 | 1552 C > T | R518X | 404297 | Nonsense | C-Terminal | 24 |
| Exon 12 | 1553 G > A | R518Q* | 404298 | Missense | C-Terminal | 1 |
| Exon 12 | 1559 T > G | M520R | 404304 | Missense | C-Terminal | 3 |
| Exon 12 | 1565 A > C | Y522S* | 404310 | Missense | C-Terminal | 1 |
| Exon 12 | 1571 T > G | V524G | 404316 | Missense | C-Terminal | 1 |
| Exon 12 | 1573 G > A | A525T | 404318 | Missense | C-Terminal | 1 |
| Exon 12 | 1574 C > T | A525V | 404319 | Missense | C-Terminal | 1 |
| Exon 12 | 1588 C > T | Q530X | 404333 | Nonsense | C-Terminal | 10 |
| Exon 13 | 1591 C > T | Q531X* | 411376 | Nonsense/Splice | C-Terminal | 1 |
| Exon 13 | 1597 C > T | R533W | 411382 | Missense | C-Terminal | 2 |
| Exon 13 | 1615 C > T | R539W | 411400 | Missense | C-Terminal | 6 |
| Exon 13 | 1616 G > A | R539Q* | 411401 | Missense | C-Terminal | 1 |
| Exon 13 | 1621 G > A | V541I* | 411406 | Missense | C-Terminal | 1 |
| Exon 13 | 1627 G > A | E543K* | 411412 | Missense | C-Terminal | 1 |
| Exon 13 | 1637 C > T | S546L | 411422 | Missense | C-Terminal | 4 |
| Exon 13 | 1640 A > G | Q547R* | 411425 | Missense | C-Terminal | 1 |
| Exon 13 | 1663 C > A | R555S* | 411448 | Missense | C-Terminal | 1 |
| Exon 13 | 1663 C > T | R555C | 411448 | Missense | C-Terminal | 4 |
| Exon 13 | 1664 G > A | R555H | 411449 | Missense | C-Terminal | 1 |
| Exon 13 | 1669 A > G | K557E | 411454 | Missense | C-Terminal | 1 |
| Intron 13 | 1686 − 1 G > T | | 412401 | Splice site | C-Terminal | 1 |
| Exon 14 | 1696 T > C | S566P* | 412412 | Missense | C-Terminal | 1 |
| Exon 14 | 1697 C > T | S566F | 412413 | Missense | C-Terminal | 5 |
| Exon 14 | 1697 C > A | S566Y | 412413 | Missense | C-Terminal | 2 |
| Exon 14 | 1700 T > C | I567T | 412416 | Missense | C-Terminal | 3 |
| Exon 14 | 1702 G > A | G568R | 412418 | Missense | C-Terminal | 7 |
| Exon 14 | 1705 A > G | K569E* | 412421 | Missense | C-Terminal | 1 |
| Exon 14 | 1712 C > T | S571L* | 412428 | Missense | C-Terminal | 1 |
| Exon 15 | 1760 C > T | T587M | 413419 | Missense | C-Terminal | 2 |
| Exon 15 | 1766 G > A | G589D | 413425 | Missense | SAR | 1 |
| Exon 15 | 1771 C > T | R591C | 413430 | Missense | SAR | 1 |
| Exon 15 | 1772 G > A | R591H | 413431 | Missense | SAR | 7 |
| Exon 15 | 1781 G > A | R594Q | 413440 | Missense | SAR | 15 |
| Exon 15 | 1781 G > C | R594P | 413440 | Missense | SAR | 1 |
| Exon 15 | 1786_1788delAGA | 596delE* | 413447 | In-frame del | SAR | 1 |
| Exon 15 | 1786 G > A | E596K* | 413445 | Missense | SAR | 1 |
| Exon 15 | 1794 G > A | K598K* | 413453 | Silent/Splice | SAR | 2 |
| Intron 15 | 1794 + 1 G > T | | 413454 | Splice site | SAR | 1 |
| Exon 16 | 1799 C > T | T600M | 483187 | Missense | SAR | 3 |
| Exon 16 | 1811insC | D603fs + 47X* | 483199 | Frame shift | SAR | 1 |
| Exon 16 | 1831 G > A | D611N* | 483219 | Missense | SAR | 1 |
| Exon 16 | 1842_1844delCCA | 614delH* | 483230 | In-frame del | SAR | 1 |
| Exon 16 | 1876 G > A | G626S | 483264 | Missense | C-Terminal | 1 |
| Exon 16 | 1894insC | P631fs + 19X | 483282 | Frame shift | C-Terminal | 1 |
| Exon 16 | 1903 G > A | G635R* | 483291 | Missense | C-Terminal | 2 |
| Exon 16 | 1986 C > G | Y662X* | 483374 | Nonsense | C-Terminal | 1 |

*denotes a novel variant, unique to this cohort. Deletion variants are indicated as del, insertions as ins, duplications as dup, and frameshift mutations are annotated for example as R174fs + 105X format, where R174 represents the last properly encoded amino acid followed by a frameshift (fs) in the coding sequence resulting in 105 miscoded amino acids leading up to a premature stop codon (X). SAR = subunit assembly region.

TABLE 2

Summary of putative LQT2-associated mutations in KCNH2

| Region | Nucleotide | Variant | Position in SEQ ID NO: 2 | Mutation Type | Location | No. of patients |
|---|---|---|---|---|---|---|
| Exon 1 | 47 A > C | D16A* | 4060 | Missense | N-Terminal | 1 |
| Exon 1 | 58 C > G | R20G* | 4071 | Missense | N-Terminal | 1 |
| Exon 1 | 73delC | G24fs + 34X* | 4086 | Frame shift | N-Terminal | 1 |
| Exon 2 | 87 C > A | F29L | 6996 | Missense | N-Terminal | 1 |
| Exon 2 | 89 T > C | I30T* | 6998 | Missense | N-Terminal | 1 |

TABLE 2-continued

Summary of putative LQT2-associated mutations in KCNH2

| Region | Nucleotide | Variant | Position in SEQ ID NO: 2 | Mutation Type | Location | No. of patients |
|---|---|---|---|---|---|---|
| Exon 2 | 94 G > A | A32T* | 7003 | Missense | N-Terminal | 1 |
| Exon 2 | 100delG | N33fs + 25X* | 7009 | Frame shift | N-Terminal | 1 |
| Exon 2 | 121 G > T | V41F* | 7030 | Missense | PAS | 1 |
| Exon 2 | 133 A > T | N45Y* | 7042 | Missense | PAS | 1 |
| Exon 2 | 158 G > A | G53D* | 7067 | Missense | PAS | 1 |
| Exon 2 | 160 T > C | Y54H* | 7069 | Missense | PAS | 1 |
| Exon 2 | 169 G > C | A57P* | 7078 | Missense | PAS | 1 |
| Exon 2 | 192 C > G | C64W* | 7101 | Missense | PAS | 1 |
| Exon 2 | 208 C > A | H70N* | 7117 | Missense | PAS | 1 |
| Exon 2 | 209 A > G | H70R | 7118 | Missense | PAS | 4 |
| Exon 2 | 215_239del; insGGCCCGT | 72_80del; insRPV* | Del: 7124 to 7148 | In-frame indel | N-Terminal | 1 |
| Exon 2 | 215 C > T | P72L* | 7124 | Missense | N-Terminal | 1 |
| Exon 2 | 215 C > A | P72Q | 7124 | Missense | N-Terminal | 10 |
| Exon 2 | 219_226delCACGCAGCinsT | R73fs + 39X* | 7128 | Frame shift | N-Terminal | 1 |
| Exon 2 | 220 A > C | T74P* | 7129 | Missense | N-Terminal | 1 |
| Exon 2 | 221 C > G | T74R* | 7130 | Missense | N-Terminal | 1 |
| Exon 2 | 221 C > T | T74M | 7130 | Missense | N-Terminal | 1 |
| Exon 2 | 234_241delTGCCGCGC | A78fs + 62X* | 7143 | Frame shift | N-Terminal | 2 |
| Exon 2 | 254 C > T | A85V | 7163 | Missense | N-Terminal | 1 |
| Exon 2 | 257 T > C | L86P* | 7166 | Missense | N-Terminal | 1 |
| Exon 2 | 281 T > G | V94G* | 7190 | Missense | PAC | 1 |
| Exon 2 | 298 C > T | R100W* | 7207 | Missense | PAC | 2 |
| Exon 2 | 299 G > A | R100Q | 7208 | Missense | PAC | 1 |
| Exon 2 | 305 A > C | D102A* | 7214 | Missense | PAC | 1 |
| Exon 3 | 317 T > A | F106Y* | 10326 | Missense | PAC | 1 |
| Exon 3 | 322 T > C | C108R* | 10331 | Missense | PAC | 1 |
| Exon 3 | 340 C > T | P114S | 10349 | Missense | PAC | 1 |
| Exon 3 | 374 T > G | F125C* | 10383 | Missense | PAC | 1 |
| Exon 3 | 376_387del | 126_129del | Del: 10385 to 10396 | In-frame del | PAC | 1 |
| Exon 3 | 422 C > T | P141L* | 10431 | Missense | PAC | 2 |
| Exon 3 | 446 G > C | G149A* | 10455 | Missense | N-Terminal | 1 |
| Exon 3 | 447insG | P151fs + 179X | 10456 | Frame shift | N-Terminal | 1 |
| Exon 3 | 454insC | P151fs + 179X | 10463 | Frame shift | N-Terminal | 1 |
| Intron 3 | 473 − 7 C > A | | 11544 | Splice site | N-Terminal | 1 |
| Exon 4 | 491 G > A | R164H* | 11569 | Missense | N-Terminal | 2 |
| Exon 4 | 506delC | P168fs + 4X* | 11584 | Frame shift | N-Terminal | 1 |
| Exon 4 | 545 C > A | S182X | 11623 | Nonsense | N-Terminal | 2 |
| Exon 4 | 548delG | S182fs + 17X* | 11626 | Frame shift | N-Terminal | 1 |
| Exon 4 | 569_586insGCGCGGGCGGCGCGGGCG (SEQ ID NO: 7) | 190_195 insGAG GAG* (SEQ ID NO: 8) | Ins: 11647 | In-frame ins | N-Terminal | 1 |
| Exon 4 | 640 G > T | E214X* | 11718 | Nonsense | N-Terminal | 1 |
| Exon 4 | 652 A > G | M218V* | 11730 | Missense | N-Terminal | 1 |
| Exon 4 | 685 G > T | E229X | 11763 | Nonsense | N-Terminal | 1 |
| Exon 4 | 724 C > G | R242G* | 11802 | Missense | N-Terminal | 1 |
| Exon 4 | 759_760delGC | A253fs + 76X* | 11837 | Frame shift | N-Terminal | 1 |
| Exon 4 | 775 G > A | D259N | 11853 | Missense | N-Terminal | 1 |
| Exon 4 | 830 C > A | A277D* | 11908 | Missense | N-Terminal | 1 |
| Exon 4 | 872 T > C | M291T* | 11950 | Missense | N-Terminal | 2 |
| Exon 4 | 902 G > T | R301L* | 11980 | Missense | N-Terminal | 1 |
| Exon 5 | 925delC | M308fs + 50X* | 12559 | Frame shift | N-Terminal | 2 |
| Exon 5 | 934 C > T | R312C | 12568 | Missense | N-Terminal | 1 |
| Exon 5 | 940 G > A | G314S* | 12574 | Missense | N-Terminal | 1 |
| Exon 5 | 967 G > A | D323N* | 12601 | Missense | N-Terminal | 1 |
| Exon 5 | 982 C > T | R328C | 12616 | Missense | N-Terminal | 4 |
| Exon 5 | 1006delA | Q335fs + 23X* | 12640 | Frame shift | N-Terminal | 1 |
| Exon 5 | 1096 C > T | R366X | 12730 | Nonsense | N-Terminal | 2 |
| Exon 5 | 1128 G > A | Q376Q | 12762 | Silent/Splice | N-Terminal | 3 |
| Exon 6 | 1138delC | S379fs + 53X* | 15872 | Frame shift | N-Terminal | 1 |
| Exon 6 | 1139delT | S379fs + 53X* | 15873 | Frame shift | N-Terminal | 1 |
| Exon 6 | 1193 G > A | W398X* | 15927 | Nonsense | N-Terminal | 1 |
| Exon 6 | 1205 A > G | H402R* | 15939 | Missense | N-Terminal | 1 |
| Exon 6 | 1262 C > T | T421M | 15996 | Missense | S1 Domain | 1 |
| Exon 6 | 1266delT | A422fs + 10X* | 16000 | Frame shift | S1 Domain | 1 |
| Exon 6 | 1280 A > G | Y427C* | 16014 | Missense | S1/S2 | 1 |
| Exon 6 | 1293 C > A | F431L* | 16027 | Missense | S1/S2 | 1 |
| Exon 6 | 1316delG | E438fs + 81X* | 16050 | Frame shift | S1/S2 | 1 |
| Exon 6 | 1319 C > T | P440L* | 16053 | Missense | S1/S2 | 1 |

TABLE 2-continued

Summary of putative LQT2-associated mutations in KCNH2

| Region | Nucleotide | Variant | Position in SEQ ID NO: 2 | Mutation Type | Location | No. of patients |
|---|---|---|---|---|---|---|
| Exon 6 | 1341 C > A | Y447X | 16075 | Nonsense | S1/S2 | 1 |
| Exon 6 | 1348 C > T | Q450X* | 16082 | Nonsense | S1/S2 | 1 |
| Exon 6 | 1352 C > T | P451L | 16086 | Missense | S2 Domain | 1 |
| Exon 6 | 1379delA | V459fs + 60X | 16113 | Frame shift | S2 Domain | 3 |
| Exon 6 | 1396 G > T | D466Y* | 16130 | Missense | S2 Domain | 1 |
| Exon 6 | 1418 C > A | T473N* | 16152 | Missense | S2/S3 | 1 |
| Exon 6 | 1419_1472 del; insA | T473fs + 26X* | Del: 16153 to 16206 | Frame shift | S2/S3 | 1 |
| Exon 6 | 1424 A > G | Y475C | 16158 | Missense | S2/S3 | 1 |
| Exon 6 | 1426 G > A | V476I* | 16160 | Missense | S2/S3 | 1 |
| Exon 6 | 1468 G > A | A490T | 16202 | Missense | S2/S3 | 1 |
| Exon 6 | 1478 A > G | Y493C | 16212 | Missense | S2/S3 | 2 |
| Exon 6 | 1478 A > C | Y493S* | 16212 | Missense | S2/S3 | 1 |
| Exon 6 | 1501 G > A | D501N | 16235 | Missense | S3 Domain | 2 |
| Intron 6 | 1557 + 1 G > C | | 16292 | Splice site | S3/S4 | 2 |
| Exon 7 | 1591 C > T | R531W* | 16914 | Missense | S4 Domain | 2 |
| Exon 7 | 1600 C > T | R534C | 16923 | Missense | S4 Domain | 4 |
| Exon 7 | 1601 G > T | R534L | 16924 | Missense | S4 Domain | 1 |
| Exon 7 | 1613_1619del AGCTGGA | R537fs + 24X | 16936 | Frame shift | S4 Domain | 1 |
| Exon 7 | 1655 T > C | L552S | 16978 | Missense | S5 domain | 2 |
| Exon 7 | 1673 C > A | A558E* | 16996 | Missense | S5 domain | 1 |
| Exon 7 | 1681 G > A | A561T | 17004 | Missense | S5 domain | 1 |
| Exon 7 | 1682 C > T | A561V | 17005 | Missense | S5 domain | 6 |
| Exon 7 | 1685 A > G | H562R* | 17008 | Missense | S5 domain | 2 |
| Exon 7 | 1688 G > A | W563X | 17011 | Nonsense | S5 domain | 1 |
| Exon 7 | 1693 G > A | A565T* | 17016 | Missense | S5 domain | 1 |
| Exon 7 | 1704 G > A | W568X* | 17027 | Nonsense | S5 domain | 1 |
| Exon 7 | 1714 G > A | G572S | 17037 | Missense | S5/Pore | 2 |
| Exon 7 | 1715 G > T | G572V* | 17038 | Missense | S5/Pore | 1 |
| Exon 7 | 1715 G > A | G572D | 17038 | Missense | S5/Pore | 1 |
| Exon 7 | 1742 C > A | S581X* | 17065 | Nonsense | S5/Pore | 1 |
| Exon 7 | 1744 C > T | R582C | 17067 | Missense | S5/Pore | 1 |
| Exon 7 | 1750 G > A | G584S | 17073 | Missense | S5/Pore | 4 |
| Exon 7 | 1750 G > C | G584R* | 17073 | Missense | S5/Pore | 1 |
| Exon 7 | 1755 G > T | W585C | 17078 | Missense | S5/Pore | 1 |
| Exon 7 | 1778 T > A | I593K* | 17101 | Missense | S5/Pore | 1 |
| Exon 7 | 1781 G > A | G594D* | 17104 | Missense | S5/Pore | 2 |
| Exon 7 | 1787 C > A | P596H* | 17110 | Missense | S5/Pore | 1 |
| Exon 7 | 1787 C > T | P596L | 17110 | Missense | S5/Pore | 1 |
| Exon 7 | 1790 A > G | Y597C | 17113 | Missense | S5/Pore | 1 |
| Exon 7 | 1797 C > A | S599R* | 17120 | Missense | S5/Pore | 1 |
| Exon 7 | 1801 G > T | G601C | 17124 | Missense | S5/Pore | 1 |
| Exon 7 | 1801 G > A | G601S | 17124 | Missense | S5/Pore | 2 |
| Exon 7 | 1810 G > A | G604S | 17133 | Missense | S5/Pore | 2 |
| Exon 7 | 1813 C > T | P605S* | 17136 | Missense | S5/Pore | 1 |
| Exon 7 | 1814 C > T | P605L* | 17137 | Missense | S5/Pore | 1 |
| Exon 7 | 1826 A > G | D609G | 17149 | Missense | S5/Pore | 1 |
| Exon 7 | 1838 C > T | T613M | 17161 | Missense | Pore | 7 |
| Exon 7 | 1841 C > T | A614V | 17164 | Missense | Pore | 6 |
| Exon 7 | 1847 A > G | Y616C* | 17170 | Missense | Pore | 1 |
| Exon 7 | 1877 G > A | G626D* | 17200 | Missense | Pore | 1 |
| Exon 7 | 1882 G > A | G628S | 17205 | Missense | Pore | 4 |
| Exon 7 | 1886 A > T | N629I* | 17209 | Missense | Pore | 2 |
| Exon 7 | 1886 A > G | N629S | 17209 | Missense | Pore | 1 |
| Exon 7 | 1901 C > T | T634I* | 17224 | Missense | Pore/S6 | 1 |
| Exon 7 | 1903 A > G | N635D* | 17226 | Missense | Pore/S6 | 1 |
| Exon 7 | 1905 C > G | N635K* | 17228 | Missense | Pore/S6 | 1 |
| Exon 7 | 1911 G > C | E637D | 17234 | Missense | Pore/S6 | 1 |
| Exon 7 | 1913_1915 delAGA | 638delK* | 17236 | In-frame del | Pore/S6 | 1 |
| Exon 7 | 1914 G > T | K638N* | 17237 | Missense | Pore/S6 | 1 |
| Exon 7 | 1930 G > C | V644L* | 17253 | Missense | S6 | 1 |
| Exon 7 | 1930 G > T | V644F | 17253 | Missense | S6 | 1 |
| Exon 7 | 1935 G > A | M645I* | 17258 | Missense | S6 | 1 |
| Exon 7 | 1942 G > A | G648S* | 17265 | Missense | S6 | 1 |
| Exon 8 | 1955delAT GCTAinsT | M651fs + 68X* | 17605 | Frame shift | S6 | 1 |
| Exon 8 | 1956delT | M651fs + X* | 17606 | Frame shift | S6 | 1 |
| Exon 8 | 1969 G > C | G657R* | 17619 | Missense | S6 | 1 |
| Exon 8 | 1969 G > A | G657S* | 17619 | Missense | S6 | 1 |
| Exon 8 | 1979 C > T | S660L | 17629 | Missense | C-Terminal | 3 |
| Exon 8 | 1985 T > C | I662T* | 17635 | Missense | C-Terminal | 1 |
| Exon 8 | 2033 T > C | L678P* | 17683 | Missense | C-Terminal | 1 |

TABLE 2-continued

Summary of putative LQT2-associated mutations in KCNH2

| Region | Nucleotide | Variant | Position in SEQ ID NO: 2 | Mutation Type | Location | No. of patients |
|---|---|---|---|---|---|---|
| Exon 8 | 2059 C > T | H687Y* | 17709 | Missense | C-Terminal | 1 |
| Exon 8 | 2078 T > C | L693P* | 17728 | Missense | C-Terminal | 1 |
| Exon 8 | 2131 A > G | I711V* | 17781 | Missense | C-Terminal | 1 |
| Exon 8 | 2145 G > A | A715A* | 17795 | Silent/Splice | C-Terminal | 3 |
| Intron 8 | 2146 − 2 A > G | | 18294 | Splice site | C-Terminal | 1 |
| Exon 9 | 2156delG | K718fs + 13X* | 18306 | Frame shift | C-Terminal | 1 |
| Exon 9 | 2182 A > T | I728F* | 18332 | Missense | C-Terminal | 2 |
| Exon 9 | 2230 C > T | R744X | 18380 | Nonsense | cNBD | 4 |
| Exon 9 | 2246 G > T | G749V* | 18396 | Missense | cNBD | 1 |
| Exon 9 | 2260_2270 dupGCCTTCGGGCC (SEQ ID NO: 9) | A753fs + 6X* | Dup. of 18399 to 18409 at 18410 | Frame shift | cNBD | 1 |
| Exon 9 | 2271 G > C | K757N* | 18421 | Missense | cNBD | 1 |
| Exon 9 | 2299 G > T | D767Y* | 18449 | Missense | cNBD | 1 |
| Exon 9 | 2309 T > C | V770A* | 18459 | Missense | cNBD | 1 |
| Exon 9 | 2320 G > T | D774Y | 18470 | Missense | cNBD | 1 |
| Exon 9 | 2362 G > A | E788K* | 18512 | Missense | cNBD | 1 |
| Exon 9 | 2371_2397del | 791_799del | Del: 18521 to 18547 | In-frame del | cNBD | 1 |
| Exon 9 | 2371 C > T | R791W | 18521 | Missense | cNBD | 1 |
| Intron 9 | 2398 + 1 G > T | | 18549 | Splice site | cNBD | 3 |
| Intron 9 | 2398 + 5 G > T | | 18553 | Splice site | cNBD | 4 |
| Exon 10 | 2417 G > A | G806E* | 19685 | Missense | cNBD | 1 |
| Exon 10 | 2419delG | G806fs + 2X* | 19687 | Frame shift | cNBD | 1 |
| Exon 10 | 2464 G > A | V822M | 19732 | Missense | cNBD | 1 |
| Exon 10 | 2467 C > T | R823W | 19735 | Missense | cNBD | 5 |
| Exon 10 | 2494 A > T | K832X* | 19762 | Nonsense | cNBD | 1 |
| Exon 10 | 2509 G > T | D837Y* | 19777 | Missense | cNBD | 1 |
| Exon 10 | 2536 C > T | P846S* | 19804 | Missense | C-Terminal | 1 |
| Exon 10 | 2587 C > T | R863X | 19855 | Nonsense | C-Terminal | 3 |
| Exon 11 | 2653 C > T | R885C | 20233 | Missense | C-Terminal | 1 |
| Exon 11 | 2660_2664 insCAAGC | K886fs + 88X* | 20240 | Frame shift | C-Terminal | 2 |
| Exon 11 | 2680 C > T | R894C* | 20260 | Missense | C-Terminal | 1 |
| Exon 11 | 2681_2685 dupCAGGC | R893fs + 81X* | 20261 | Frame shift | C-Terminal | 1 |
| Exon 11 | 2681 G > T | R894L* | 20261 | Missense | C-Terminal | 1 |
| Intron 11 | 2692 + 1_29 62 + 6insACACGG | | 20273 | Splice site | C-Terminal | 1 |
| Exon 12 | 2707 G > A | G903R* | 20852 | Missense | C-Terminal | 3 |
| Exon 12 | 2717 C > T | S906L* | 20862 | Missense | C-Terminal | 2 |
| | 2722_2725 dupGGCC | A907fs + 12X* | 20867 | Frame shift | C-Terminal | 1 |
| Exon 12 | 2729_2744del | G909fs + 58X* | Del: 20874 to 20889 | Frame shift | C-Terminal | 1 |
| Exon 12 | 2736_2751del | R912fs + 55X* | Del: 20881 to 20896 | Frame shift | C-Terminal | 1 |
| Exon 12 | 2738 C > T | A913V | 20883 | Missense | C-Terminal | 5 |
| Exon 12 | 2739dupCGGGC | G914fs + 60X* | 20884 | Frame shift | C-Terminal | 1 |
| Exon 12 | 2758 C > T | R920W* | 20903 | Missense | C-Terminal | 1 |
| Exon 12 | 2759 G > A | R920Q* | 20904 | Missense | C-Terminal | 1 |
| Exon 12 | 2765 G > A | R922Q* | 20910 | Missense | C-Terminal | 1 |
| Exon 12 | 2771 G > A | G924E* | 20916 | Missense | C-Terminal | 1 |
| Exon 12 | 2771 G > C | G924A* | 20916 | Missense | C-Terminal | 1 |
| Exon 12 | 2780 G > A | W927X | 20925 | Nonsense | C-Terminal | 1 |
| Exon 12 | 2784delG | G928fs + 44X* | 20930 | Frame shift | C-Terminal | 1 |
| Exon 12 | 2810 G > A | S937N* | 20955 | Missense | C-Terminal | 1 |
| Exon 12 | 2892delC | P964fs + 8X* | 21037 | Frame shift | C-Terminal | 1 |
| Exon 12 | 2893insC | P964fs + 153X* | 21038 | Frame shift | C-Terminal | 1 |
| Exon 12 | 2918_2920 insCC | P972fs + 1X* | 21063 | Frame shift | C-Terminal | 1 |
| Exon 12 | 2959_2960 delCT | P986fs + 130X | 21104 | Frame shift | C-Terminal | 1 |
| Exon 13 | 3002insT | F1000fs + 117X* | 21238 | Frame shift | C-Terminal | 1 |
| Exon 13 | 3002 G > A | W1001X | 21238 | Nonsense | C-Terminal | 5 |
| Exon 13 | 3014 G > A | R1005Q* | 21250 | Missense | C-Terminal | 1 |
| Exon 13 | 3020 G > A | R1007H* | 21256 | Missense | C-Terminal | 1 |
| Exon 13 | 3032delA | Q1010fs + 45X* | 21268 | Frame shift | C-Terminal | 1 |
| Exon 13 | 3040 C > T | R1014X | 21276 | Nonsense | C-Terminal | 1 |
| Exon 13 | 3088_3089 dupGC | S1029fs + 27X* | 21324 | Frame shift | C-Terminal | 1 |
| Exon 13 | 3093_3106del | R1033fs + 79X* | Del: 21329 to 21342 | Frame shift | C-Terminal | 1 |

TABLE 2-continued

Summary of putative LQT2-associated mutations in KCNH2

| Region | Nucleotide | Variant | Position in SEQ ID NO: 2 | Mutation Type | Location | No. of patients |
|---|---|---|---|---|---|---|
| Exon 13 | 3093dupGGGT | G1031fs + 87X* | 21330 | Frame shift | C-Terminal | 1 |
| Exon 13 | 3094delC | G1031fs + 24X | 21330 | Frame shift | C-Terminal | 1 |
| Exon 13 | 3097 C > T | R1033W* | 21333 | Missense | C-Terminal | 1 |
| Exon 13 | 3098insC | R1032fs + 85X* | 21334 | Frame shift | C-Terminal | 1 |
| Exon 13 | 3099_3112del | R1033fs + 79X* | Del: 21335 to 21348 | Frame shift | C-Terminal | 1 |
| Exon 13 | 3099delG | P1034fs + 21X | 21335 | Frame shift | C-Terminal | 1 |
| Exon 13 | 3099_3100 insCG | R1033fs + 23X* | 21335 | Frame shift | C-Terminal | 1 |
| Exon 13 | 3100_3107 delCCCCG GGGinsGGC | R1033fs + 82X* | 21336 | Frame shift | C-Terminal | 1 |
| Exon 13 | 3101_3108 delCCCGGGGC | R1033fs + 81X* | 21337 | Frame shift | C-Terminal | 1 |
| Exon 13 | 3101_3103 insGGC | 1034insR* | 21337 | In-frame ins | C-Terminal | 1 |
| Exon 13 | 3102_3111del | P1034fs + 18X* | Del: 21338 to 21347 | Frame shift | C-Terminal | 1 |
| Exon 13 | 3103delC | P1034fs + 21X | 21339 | Frame shift | C-Terminal | 2 |
| Exon 13 | 3104insC | P1034fs + 83X* | 21340 | Frame shift | C-Terminal | 2 |
| Exon 13 | 3108insG | G1036fs + 81X | 21344 | Frame shift | C-Terminal | 3 |
| Exon 13 | 3112 G > A | V1038M* | 21348 | Missense | C-Terminal | 1 |
| Exon 13 | 3113_3126 dupGCCCCG GGGCGACG (SEQ ID NO: 10) | D1037fs + 23X* | Dup. of 21335 to 21348 at 21349 | Frame shift | C-Terminal | 1 |
| Exon 13 | 3146 T > C | L1049P* | 21382 | Missense | C-Terminal | 1 |
| Exon 14 | 3196 C > G | L1066V* | 21705 | Missense | C-Terminal | 1 |
| Exon 14 | 3233 A > G | Y1078C* | 21742 | Missense | C-Terminal | 1 |
| Exon 14 | 3234delC | A1077fs + X* | 21743 | Frame shift | C-Terminal | 1 |
| Exon 14 | 3256insG | G1085fs + 32X* | 21765 | Frame shift | C-Terminal | 1 |
| Exon 14 | 3278 C > T | P1093L* | 21787 | Missense | C-Terminal | 2 |
| Exon 15 | 3343 A > G | M1115V* | 23214 | Missense | C-Terminal | 1 |
| Exon 15 | 3407_3410 dupCGCC | R1135fs + 134X* | 23278 | Frame shift | C-Terminal | 1 |
| Exon 15 | 3471insC | G1158fs + 110X* | 23342 | Frame shift | C-Terminal | 1 |

*denotes a novel variant, unique to this cohort. Deletion variants are indicated as "del", insertions as ins, duplications as "dup", and frameshift mutations are designated by "fs".

TABLE 3

Summary of putative LQT3-associated mutations in SCN5A

| Region | Nucleotide | Variant | Position in SEQ ID NO: 3 | Mutation Type | Location Type | No. of patients |
|---|---|---|---|---|---|---|
| Exon 2 | 53 G > A | R18Q* | 141435 | Missense | N-terminal | 1 |
| Exon 2 | 80 G > A | R27H | 141408 | Missense | N-terminal | 1 |
| Exon 2 | 89 A > G | E30G* | 141399 | Missense | N-terminal | 1 |
| Exon 2 | 128 G > A | R43Q | 141360 | Missense | N-terminal | 1 |
| Exon 2 | 142 G > A | E48K* | 141346 | Missense | N-terminal | 1 |
| Exon 2 | 154 C > T | P52S* | 141334 | Missense | N-terminal | 1 |
| Exon 2 | 158 G > A | R53Q* | 141330 | Missense | N-terminal | 1 |
| Exon 2 | 217 C > T | Q73X* | 141271 | Nonsense | N-terminal | 1 |
| Exon 3 | 310 C > G | R104Q* | 138573 | Missense | N-terminal | 1 |
| Exon 3 | 343 A > G | S115G* | 138540 | Missense | N-terminal | 1 |
| Exon 3 | 373 G > C | V125L | 138510 | Missense | N-terminal | 1 |
| Exon 5 | 535 C > T | R179X | 129099 | Nonsense | DI-S2/S3 | 1 |
| Exon 6 | 635 T > C | L212P | 121991 | Missense | DI-S3/S4 | 1 |
| Exon 6 | 664 C > T | R222X | 121962 | Nonsense | DI-S4 | 1 |
| Exon 6 | 665 G > A | R222Q* | 121961 | Missense | DI-S4 | 1 |
| Exon 6 | 673 C > T | R225W | 121953 | Missense | DI-S4 | 4 |
| Exon 7 | 718 G > A | V240M* | 118130 | Missense | DI-S4/S5 | 1 |
| Exon 7 | 739 G > C | V247L* | 118109 | Missense | DI-S4/S5 | 1 |
| Exon 7 | 825 C > A | N275K | 118023 | Missense | DI-S5 | 1 |
| Exon 7 | 865 G > A | G289S* | 117983 | Missense | DI-S5/S6 | 1 |
| Exon 9 | 1018 C > T | R340W* | 114971 | Missense | DI-S5/S6 | 1 |
| Exon 9 | 1099 C > T | R367C | 114890 | Missense | DI-S5/S6 | 2 |
| Exon 9 | 1109 C > T | T370M | 114880 | Missense | DI-S5/S6 | 1 |
| Exon 10 | 1167 C > A | Y389X* | 114302 | Nonsense | DI-S5/S6 | 1 |
| Exon 10 | 1190 T > C | I397T* | 114279 | Missense | DI-S6 | 1 |

TABLE 3-continued

Summary of putative LQT3-associated mutations in SCN5A

| Region | Nucleotide | Variant | Position in SEQ ID NO: 3 | Mutation Type | Location Type | No. of patients |
|---|---|---|---|---|---|---|
| Exon 10 | 1218 C > G | N406K | 114251 | Missense | DI-S6 | 1 |
| Exon 10 | 1225 C > G | L409V* | 114244 | Missense | DI-S6 | 1 |
| Exon 10 | 1231 G > A | V411M | 114238 | Missense | DI-S6 | 3 |
| Exon 10 | 1285_1287 delGAG | 429delE* | 114182 | In-frame del | DI/DII | 1 |
| Exon 11 | 1385 A > C | E462A* | 113042 | Missense | DI/DII | 1 |
| Exon 12 | 1588 T > G | F530V* | 112194 | Missense | DI/DII | 1 |
| Exon 12 | 1604 G > A | R535Q* | 112178 | Missense | DI/DII | 2 |
| Exon 12 | 1705 C > T | R569W* | 112077 | Missense | DI/DII | 1 |
| Exon 12 | 1712 G > T | S571I* | 112070 | Missense | DI/DII | 1 |
| Exon 12 | 1714 G > T | A572S* | 112068 | Missense | DI/DII | 2 |
| Exon 12 | 1715 C > T | A572V* | 112067 | Missense | DI/DII | 2 |
| Exon 12 | 1756_1761 delGCCCTC | 586_587delAL* | 112021 | In-frame del | DI/DII | 1 |
| Exon 12 | 1844 G > A | G615E | 111938 | Missense | DI/DII | 5 |
| Exon 13 | 1915 G > A | G639R | 107206 | Missense | DI/DII | 1 |
| Exon 13 | 1960 G > A | E654K* | 107161 | Missense | DI/DII | 1 |
| Exon 13 | 2018 T > C | L673P* | 107103 | Missense | DI/DII | 1 |
| Exon 14 | 2065 C > T | R689C* | 106106 | Missense | DI/DII | 1 |
| Exon 14 | 2102 C > T | P701L | 106069 | Missense | DI/DII | 1 |
| Exon 14 | 2192 C > T | T731I* | 105979 | Missense | DII-S1 | 1 |
| Exon 14 | 2249 A > G | Q750R* | 105922 | Missense | DII-S2 | 1 |
| Exon 15 | 2314 G > A | D772N | 95702 | Missense | DII-S2/S3 | 1 |
| Exon 16 | 2447 T > A | F816Y* | 94211 | Missense | DII-S4 | 1 |
| Exon 16 | 2542 A > T | I848F* | 94116 | Missense | DII-S5 | 1 |
| Exon 16 | 2552_2553 dupGT | V850fs + 18X* | 94107 | Frame shift | DII-S5 | 1 |
| Exon 17 | 2878 C > A | Q960K* | 89461 | Missense | DII/DIII | 1 |
| Exon 17 | 2894 G > T | R965L* | 89445 | Missense | DII/DIII | 1 |
| Exon 17 | 2942 G > T | C981F* | 89397 | Missense | DII/DIII | 1 |
| Exon 17 | 2989 G > T | A997S | 89350 | Missense | DII/DIII | 1 |
| Exon 17 | 3010 T > C | C1004R* | 89329 | Missense | DII/DIII | 1 |
| Exon 17 | 3157 G > A | E1053K | 89182 | Missense | DII/DIII | 1 |
| Exon 17 | 3206 C > T | T1069M | 89133 | Missense | DII/DIII | 1 |
| Exon 18 | 3299 C > T | A1100V* | 87605 | Missense | DII/DIII | 1 |
| Exon 18 | 3340 G > A | D1114N | 87564 | Missense | DII/DIII | 1 |
| Exon 19 | 3496 G > A | D1166N* | 84856 | Missense | DII/DIII | 1 |
| Exon 20 | 3596 A > C | Y1199S* | 83547 | Missense | DII/DIII | 1 |
| Exon 20 | 3634_3636 delATC | I212delI* | 83507 | In-frame del | DIII-S1 | 1 |
| Exon 22 | 3847 C > A | L1283M* | 70711 | Missense | DIII-S3 | 1 |
| Exon 22 | 3911 C > T | T1304M | 70647 | Missense | DIII-S4 | 3 |
| Exon 23 | 3974 A > G | N1325S | 68598 | Missense | DIII-S4/S5 | 3 |
| Exon 23 | 3976 G > T | A1326S* | 68596 | Missense | DIII-S4/S5 | 1 |
| Exon 23 | 4000 A > G | I1334V* | 68572 | Missense | DIII-S4/S5 | 1 |
| Exon 23 | 4012 C > G | L1338V* | 68560 | Missense | DIII-S5 | 1 |
| Exon 24 | 4296 G > C | R1432S | 65414 | Missense | DIII-S5/S6 | 1 |
| Exon 25 | 4415 A > G | N1472S* | 64643 | Missense | DIII/DIV | 1 |
| Exon 25 | 4418 T > G | F1473C | 64640 | Missense | DIII/DIV | 1 |
| Exon 26 | 4442 G > A | G1481E | 63936 | Missense | DIII/DIV | 1 |
| Exon 26 | 4459 A > C | M1487L* | 63919 | Missense | DIII/DIV | 1 |
| Exon 26 | 4463 C > G | T1488R* | 63915 | Missense | DIII/DIV | 1 |
| Exon 26 | 4467 G > T | E1489D* | 63911 | Missense | DIII/DIV | 1 |
| Exon 26 | 4478 A > G | K1493R | 63900 | Missense | DIII/DIV | 2 |
| Exon 26 | 4484 A > C | Y1495S* | 63894 | Missense | DIII/DIV | 1 |
| Exon 26 | 4492 A > G | M1498V* | 63886 | Missense | DIII/DIV | 1 |
| Exon 26 | 4501 C > G | L1501V | 63877 | Missense | DIII/DIV | 1 |
| Exon 26 | 4515 G > T | K1505N* | 63863 | Missense | DIII/DIV | 1 |
| Exon 26 | 4519_4527 delCAGAAGCCC | 1507_1509delQKP | 63851 | In-frame del | DIII/DIV | 1 |
| Exon 27 | 4594 G > A | V1532I* | 62678 | Missense | DIV-S1 | 1 |
| Exon 27 | 4680 G > C | L1560F* | 62592 | Missense | DIV-S2 | 1 |
| Exon 27 | 4779 C > G | I1593M* | 62493 | Missense | DIV-S3 | 1 |
| Exon 27 | 4781 T > C | F1594S* | 62491 | Missense | DIV-S3 | 1 |
| Exon 27 | 4786 T > A | F1596I* | 62486 | Missense | DIV-S3 | 2 |
| Exon 28 | 4850_4852 delTCT | 1617delF | 59700 | In-frame del | DIV-S3/S4 | 1 |
| Exon 28 | 4868 G > A | R1623Q | 59684 | Missense | DIV-S4 | 2 |
| Exon 28 | 4868 G > T | R1623L | 59684 | Missense | DIV-S4 | 1 |
| Exon 28 | 4877 G > A | R1626H | 59675 | Missense | DIV-S4 | 1 |
| Exon 28 | 4930 C > T | R1644C | 59622 | Missense | DIV-S4 | 1 |
| Exon 28 | 4948 C > T | L1650F* | 59604 | Missense | DIV-S4/S5 | 1 |
| Exon 28 | 4955 T > C | MT1652* | 59597 | Missense | DIV-S4/S5 | 1 |

TABLE 3-continued

Summary of putative LQT3-associated mutations in SCN5A

| Region | Nucleotide | Variant | Position in SEQ ID NO: 3 | Mutation Type | Location Type | No. of patients |
|---|---|---|---|---|---|---|
| Exon 28 | 5168 C > A | T1723N* | 59384 | Missense | DIV-S5/S6 | 1 |
| Exon 28 | 5215 C > T | R1739W* | 59337 | Missense | DIV-S5/S6 | 1 |
| Exon 28 | 5281 C > T | L1761F* | 59271 | Missense | DIV-S6 | 1 |
| Exon 28 | 5282 T > A | L1761H* | 59270 | Missense | DIV-S6 | 1 |
| Exon 28 | 5287 G > A | V1763M | 59265 | Missense | DIV-S6 | 1 |
| Exon 28 | 5329 G > A | V1777M | 59223 | Missense | C-Terminal | 1 |
| Exon 28 | 5336 C > T | T1779M | 59216 | Missense | C-Terminal | 2 |
| Exon 28 | 5350 G > A | E1784K | 59202 | Missense | C-Terminal | 15 |
| Exon 28 | 5361_5364 del TGAG | L1786fs + 45X* | 59188 | Frame shift | C-Terminal | 1 |
| Exon 28 | 5384 A > G | Y1795C | 59168 | Missense | C-Terminal | 1 |
| Exon 28 | 5393 G > A | W1798X* | 59159 | Nonsense | C-Terminal | 1 |
| Exon 28 | 5477 G > A | R1826H | 59075 | Missense | C-Terminal | 2 |
| Exon 28 | 5516 A > G | D1839G | 59036 | Missense | C-Terminal | 1 |
| Exon 28 | 5689 C > T | R1897W* | 58863 | Missense | C-Terminal | 1 |
| Exon 28 | 5701 G > C | E1901Q* | 58851 | Missense | C-Terminal | 1 |
| Exon 28 | 5929 T > A | Y1977N* | 58623 | Missense | C-Terminal | 1 |
| Exon 28 | 6010 T > G | F2004V* | 58542 | Missense | C-Terminal | 1 |
| Exon 28 | 6034 C > T | R2012C* | 58518 | Missense | C-Terminal | 1 |

*denotes a novel variant, unique to this cohort. Deletion variants are indicated as "del", duplications as "dup", and frameshift mutations are designated by "fs".

TABLE 4

Summary of putative LQT5-associated mutations in KCNE1

| Region | Nucleotide | Variant | Position in SEQ ID NO: 4 | Mutation Type | Location | No. of patients |
|---|---|---|---|---|---|---|
| Exon 4 | 9_12delGTCT | L3fs + 4X* | 13137 | Frame shift | N-Terminal | 1 |
| Exon 4 | 13insT | S4fs + 0X* | 13134 | Frame shift | N-Terminal | 1 |
| Exon 4 | 23 C > T | A8V | 13123 | Missense | N-Terminal | 1 |
| Exon 4 | 29 C > T | T10M | 13117 | Missense | N-Terminal | 3 |
| Exon 4 | 50 G > A | W17X* | 13096 | Nonsense | N-Terminal | 1 |
| Exon 4 | 83 C > T | S28L | 13063 | Missense | N-Terminal | 2 |
| Exon 4 | 95 G > A | R32H | 13051 | Missense | N-Terminal | 1 |
| Exon 4 | 163 G > A | G55S* | 12983 | Missense | Transmembrane | 1 |
| Exon 4 | 172 A > C | T58P | 12974 | Missense | Transmembrane | 2 |
| Exon 4 | 176 T > C | L59P | 12970 | Missense | Transmembrane | 2 |
| Exon 4 | 199 C > T | R67C* | 12947 | Missense | C-Terminal | 1 |
| Exon 4 | 200 G > A | R67H* | 12946 | Missense | C-Terminal | 1 |
| Exon 4 | 209 A > T | K70M* | 12937 | Missense | C-Terminal | 1 |
| Exon 4 | 226 G > A | D76N | 12920 | Missense | C-Terminal | 9 |
| Exon 4 | 227_229del ACCinsTCTA | N75fs + 34X* | 12917 | Frame shift | C-Terminal | 1 |
| Exon 4 | 247 G > A | E83K* | 12899 | Missense | C-Terminal | 1 |
| Exon 4 | 349 C > T | Q117X* | 12797 | Nonsense | C-Terminal | 1 |
| Exon 4 | 374 C > T | T125M | 12772 | Missense | C-Terminal | 1 |

*denotes a novel variant, unique to this cohort. Deletion variants are indicated as "del", insertion as "ins", and frameshift mutations are designated by "fs".

TABLE 5

Summary of putative LQT6-associated mutations in KCNE2

| Region | Nucleotide | Variant | Position SEQ ID NO: 5 | Mutation Type | Location | No. of patients |
|---|---|---|---|---|---|---|
| Exon 2 | 40 G > A | V14I | 15735 | Missense | N-Terminal | 1 |
| Exon 2 | 59 T > A | I20N* | 15754 | Missense | N-Terminal | 1 |
| Exon 2 | 80 G > A | R27H* | 15775 | Missense | N-Terminal | 1 |
| Exon 2 | 161 T > C | M54T | 15856 | Missense | Transmembrane | 3 |
| Exon 2 | 170 T > C | I57T | 15865 | Missense | Transmembrane | 2 |
| Exon 2 | 193 G > C | V65L* | 15888 | Missense | Transmembrane | 1 |
| Exon 2 | 230 G > A | R77Q | 15925 | Missense | C-Terminal | 2 |

TABLE 5-continued

Summary of putative LQT6-associated mutations in KCNE2

| Region | Nucleotide | Variant | Position SEQ ID NO: 5 | Mutation Type | Location | No. of patients |
|---|---|---|---|---|---|---|
| Exon 2 | 281 A > G | E94G* | 15976 | Missense | C-Terminal | 1 |
| Exon 2 | 369_370delCT | P123fs + 14X* | 16064 | Frame shift | C-Terminal | 1 |

*denotes a novel variant, unique to this cohort. Deletion variants are indicated as "del" and frameshift mutations are designated by "fs".

REFERENCES

1. Crotti, L., Celano, G., Dagradi, F., and Schwartz, P. J. 2008. Congenital long QT syndrome. *Orphanet J Rare Dis* 3:18.
2. Schwartz, P. J., et al. 2009. Prevalence of the congenital long-QT syndrome. *Circulation* 120:1761-1767.
3. Wang, Q., et al. 1996. Positional cloning of a novel potassium channel gene: KVLQT1 mutations cause cardiac arrhythmias. *Nat Genet* 12:17-23.
4. Abbott, G. W., et al. 1999. MiRP1 forms IKr potassium channels with HERG and is associated with cardiac arrhythmia. *Cell* 97:175-187.
5. Mohler, P. J., et al. 2003. Ankyrin-B mutation causes type 4 long-QT cardiac arrhythmia and sudden cardiac death. *Nature* 421:634-639.
6. Splawski, I., Tristani-Firouzi, M., Lehmann, M. H., Sanguinetti, M. C., and Keating, M. T. 1997. Mutations in the hminK gene cause long QT syndrome and suppress IKs function. *Nat Genet* 17:338-340.
7. Wang, Q., et al. 1995. SCN5A mutations associated with an inherited cardiac arrhythmia, long QT syndrome. *Cell* 80:805-811.
8. Chen, L., et al. 2007. Mutation of an A-kinase-anchoring protein causes long-QT syndrome. *Proc Natl Acad Sci USA* 104:20990-20995.
9. Medeiros-Domingo, A., et al. 2007. SCN4B-encoded sodium channel beta4 subunit in congenital long-QT syndrome. *Circulation* 116:134-142.
10. Plaster, N. M., et al. 2001. Mutations in Kir2.1 cause the developmental and episodic electrical phenotypes of Andersen's syndrome. *Cell* 105:511-519.
11. Splawski, I., et al. 2004. Ca(V)1.2 calcium channel dysfunction causes a multisystem disorder including arrhythmia and autism. *Cell* 119:19-31.
12. Ueda, K., et al. 2008. Syntrophin mutation associated with long QT syndrome through activation of the nNOS-SCN5A macromolecular complex. *Proc Natl Acad Sci USA* 105:9355-9360.
13. Vatta, M., et al. 2006. Mutant caveolin-3 induces persistent late sodium current and is associated with long-QT syndrome. *Circulation* 114:2104-2112.
14. Curran, M. E., et al. 1995. A molecular basis for cardiac arrhythmia: HERG mutations cause long QT syndrome. *Cell* 80:795-803.
15. Tester, D. J., Will, M. L., Haglund, C. M., and Ackerman, M. J. 2005. Compendium of cardiac channel mutations in 541 consecutive unrelated patients referred for long QT syndrome genetic testing. *Heart Rhythm* 2:507-517.
16. Kapplinger, J. D., et al. 2009. Spectrum and prevalence of mutations from the first 2,500 consecutive unrelated patients referred for the FAMILION long QT syndrome genetic test. *Heart Rhythm* 6:1297-1303.
17. Tester, D. J., et al. 2006. Allelic dropout in long QT syndrome genetic testing: a possible mechanism underlying false-negative results. *Heart Rhythm* 3:815-821.
18. Kapa, S., et al. 2009. Genetic testing for long-QT syndrome: distinguishing pathogenic mutations from benign variants. *Circulation* 120:1752-1760.
19. Moss, A. J., et al. 2007. Clinical aspects of type-1 long-QT syndrome by location, coding type, and biophysical function of mutations involving the KCNQ1 gene. *Circulation* 115:2481-2489.
20. Moss, A. J., et al. 2002. Increased risk of arrhythmic events in long-QT syndrome with mutations in the pore region of the human ether-a-go-go-related gene potassium channel. *Circulation* 105:794-799.
21. Shimizu, W., et al. 2009. Genotype-phenotype aspects of type 2 long QT syndrome. *J Am Coll Cardiol* 54:2052-2062.

EQUIVALENTS

Those skilled in the art will recognize, or be able to ascertain using no more than routine experimentation, many equivalents to the specific embodiments of the invention described herein. Such equivalents are intended to be encompassed by the following claims. The contents of all references, patents and published patent applications cited throughout this application are incorporated herein by reference.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08658358B1). An electronic copy of the "Sequence Listing" will also be available from the USPTO upon request and payment of the fee set forth in 37 CFR 1.19(b)(3).

What is claimed is:

1. A method for determining whether a subject suffers from or is predisposed to suffer from congenital long QT syndrome (LQTS) comprising
analyzing a biological sample from a subject for the allele present at KCNQ1 mutations 1075 C>T, 190_210del (in which nucleotides 80718 to 80738 of SEQ ID NO: 1 are deleted), 862_880del (in which nucleotides 208341 to 208359 of SEQ ID NO: 1 are deleted), 1265delA, and 1338 C>G,
detecting in the biological sample any one or more of the KCNQ1 mutations 1075 C>T, 190_210del, 862_880del, 1265delA, and 1338 C>G, and
determining that the subject suffers from or is predisposed to suffer from LQTS when any one or more of the KCNQ1 mutations 1075 C>T, 190_210del, 862_880del, 1265delA, and 1338 C>G is present in the biological sample.

2. A method for detecting a KCNQ1 variant, comprising
analyzing a biological sample from a subject for the allele present at KCNQ1 mutations 1075 C>T, 190_210del (in which nucleotides 80718 to 80738 of SEQ ID NO: 1 are deleted), 862_880del (in which nucleotides 208341 to 208359 of SEQ ID NO: 1 are deleted), 1265delA, and 1338 C>G, and
detecting in the biological sample any one or more of the KCNQ1 mutations 1075 C>T, 190_210del, 862_880del, 1265delA, and 1338 C>G.

3. The method of claim 1 or 2, wherein the analyzing comprises using a technique selected from the group consisting of polymerase chain reaction (PCR) amplification reaction, reverse-transcriptase PCR analysis, single-strand conformation polymorphism analysis (SSCP), mismatch cleavage detection, heteroduplex analysis, Southern blot analysis, Western blot analysis, deoxyribonucleic acid sequencing, restriction fragment length polymorphism analysis, haplotype analysis, serotyping, and combinations or subcombinations thereof.

4. The method of claim 1 or 2, wherein the biological sample from the subject is selected from the group consisting of a fluid, blood fluids, vomit, intra-articular fluid, saliva, lymph, cystic fluid, urine, fluids collected by bronchial lavage, fluids collected by peritoneal rinsing, gynecological fluids, a blood sample or a component thereof, a tissue or component thereof, bone, connective tissue, cartilage, lung, liver, kidney, muscle tissue, heart, pancreas, and skin.

* * * * *